US012018293B2

(12) United States Patent
Hong et al.

(10) Patent No.: US 12,018,293 B2
(45) Date of Patent: Jun. 25, 2024

(54) METHOD FOR LARGE-SCALE PREPARATION OF PURIFIED PREPARATION OF RECOMBINANT LENTIVIRAL VECTOR AT GMP GRADE

(71) Applicant: ABELZETA INC., Rockville, MD (US)

(72) Inventors: Yi Hong, Shanghai (CN); Ting Yan, Shanghai (CN); Jiangguo Ying, Shanghai (CN); Haojie Zhang, Shanghai (CN); Li Zhang, Shanghai (CN); Fei Wang, Shanghai (CN); Dijun Zhao, Shanghai (CN); Luyi Zhang, Shanghai (CN)

(73) Assignee: ABELZETA INC., Rockville, MD (US)

( * ) Notice: Subject to any disclaimer, the term of this patent is extended or adjusted under 35 U.S.C. 154(b) by 895 days.

(21) Appl. No.: 17/042,125

(22) PCT Filed: Mar. 28, 2019

(86) PCT No.: PCT/CN2019/080213
§ 371 (c)(1),
(2) Date: Sep. 27, 2020

(87) PCT Pub. No.: WO2019/184995
PCT Pub. Date: Oct. 3, 2019

(65) Prior Publication Data
US 2021/0009966 A1    Jan. 14, 2021

(30) Foreign Application Priority Data

Mar. 28, 2018 (CN) .................. 201810264813.X

(51) Int. Cl.
| | |
|---|---|
| *C12N 7/02* | (2006.01) |
| *C12M 1/00* | (2006.01) |
| *C12N 7/00* | (2006.01) |
| *C12N 15/10* | (2006.01) |
| *C12N 15/86* | (2006.01) |

(52) U.S. Cl.
CPC .............. *C12N 7/02* (2013.01); *C12M 47/02* (2013.01); *C12M 47/12* (2013.01); *C12N 7/00* (2013.01); *C12N 15/101* (2013.01); *C12N 15/1017* (2013.01); *C12N 15/86* (2013.01); *C12N 2740/15021* (2013.01); *C12N 2740/15043* (2013.01); *C12N 2740/15051* (2013.01)

(58) Field of Classification Search
None
See application file for complete search history.

(56) References Cited

U.S. PATENT DOCUMENTS

| | | | |
|---|---|---|---|
| 2003/0175688 A1 | 9/2003 | Pennathur-Das et al. | |
| 2007/0249019 A1 | 10/2007 | Kang et al. | |
| 2008/0026448 A1* | 1/2008 | Lydersen ............... | A61K 39/12 |
| | | | 435/235.1 |
| 2009/0175906 A1 | 7/2009 | Kaylan et al. | |
| 2011/0207202 A1 | 8/2011 | Luitjens et al. | |
| 2014/0315294 A1 | 10/2014 | Marceau et al. | |
| 2015/0133636 A1* | 5/2015 | Xenopoulos ......... | B01D 15/363 |
| | | | 435/238 |
| 2017/0002332 A1 | 1/2017 | Boudeffa et al. | |

FOREIGN PATENT DOCUMENTS

| | | |
|---|---|---|
| CN | 103881984 A | 6/2014 |
| CN | 104371982 A | 2/2015 |
| CN | 106434571 A | 2/2017 |
| CN | 106474466 A | 3/2017 |
| CN | 107043784 A | 8/2017 |
| CN | 107384877 A | 11/2017 |
| CN | 107523555 A | 12/2017 |
| CN | 107630037 A | 1/2018 |
| CN | 107841482 A | 3/2018 |
| JP | 2009-534030 A | 9/2009 |
| JP | 2017-503486 A | 2/2017 |
| JP | 2018-507707 A | 3/2018 |
| WO | 03039459 A2 | 5/2003 |
| WO | 2013/076309 A1 | 5/2013 |
| WO | 2016/128408 A | 5/2016 |

OTHER PUBLICATIONS

CN107043784A google patents translation Aug. 15, 2017.*
Witting et al: "Efficient Large Volume Lentiviral Vector Production Using Flow Electroporation", Human Gene Therapy, 2012, vol. 23, pp. 243-249.
Jiang et al., Purification of Rotavirus by using Multimode media Capto core 700, Chinese J. Biologicals, 2015, vol. 28 No. 1, pp. 72-78.
Ansorge et al. Recent progress in lentiviral vector mass production, Biochemical Engineering Journal, 2010, vol. 48, No. 3, pp. 362-374.

(Continued)

*Primary Examiner* — Shanon A. Foley
(74) *Attorney, Agent, or Firm* — Leason Ellis LLP

(57) ABSTRACT

Provided is a method for large-scale preparation of a purified preparation of a recombinant lentiviral vector at the GMP grade. The method comprises: (a) providing raw material feed liquid to be purified that comprises recombinant viral vectors; (b) carrying out a microfiltration treatment on the feed liquid to obtain a microfiltered filtrate comprising the recombinant viral vectors; (c) optionally concentrating the filtrate to obtain a concentrated filtrate; (d) purifying the filtrate obtained in the previous step by means of chromatography to obtain a crude pure product comprising the recombinant viral vectors; and (e) subjecting the crude pure product obtained in the previous step to liquid exchange and elaborate purification to obtain the purified recombinant viral vectors.

8 Claims, No Drawings

(56) References Cited

OTHER PUBLICATIONS

International Search Report and Written Opinion in PCT/CN2019/080215, dated May 24, 2019.
U.S. Appl. No. 17/041,578 (371 of PCT/CN2019/080215 (WO2019/184996)), in Chinese and English.
Maria Mercedes Segura et al: "New developments in lentiviral vector design, production and purification", Expert Opinion on Biological Therapy, vol. 13, No. 7, 2013, pp. 987-101.
Ansorage S et al: "Development of a scalable process for high-yield lentiviral vector production by transient transfection of HEK293 suspension cultures", The Journal of Gene Medicine, vol. 11, No. 10, 2009, pp. 868-876.
Broussau et al: "Inducible Packaging Cells for Large-scale Production of Lentiviral Vectors in Serum-free Suspension Culture", Molecular Therapy, 2008, 16(3): 500-507.
Segura et al: "Production of Lentiviral Vectors by Large-Scale Transient Transfection of Suspension Cultures and Affinity Chromatography Purification", Biotechnology and Bioengineering, 2007, 98(4): 789-799.
Vanessa Bandeira et al., "Downstream Processing of Lentiviral Vectors: Releasing Bottlenecks," Human Gene Therapy Methods 23(4):255-263 (Aug. 2012), DOI: 10.1089/hgtb.2012.059.
Cai, Jingjing et al., "Lentiviral Vector Packaging and Production Method," Journal of Yangtze University (Nat Sci Edit), 11(9):121-124, Mar. 25, 2014. (D3 in ISR in Mandarin with English summary).
International Search Report in PCT/CN2019/080213, dated May 30, 2019.

\* cited by examiner

METHOD FOR LARGE-SCALE PREPARATION OF PURIFIED PREPARATION OF RECOMBINANT LENTIVIRAL VECTOR AT GMP GRADE

CROSS-REFERENCE TO RELATED APPLICATIONS

This is a U.S. national phase application under 35 U.S.C. § 371 of Patent Cooperation Treaty Application No. PCT/CN2019/080213, filed Mar. 28, 2019, which claims priority from Chinese Patent Application Serial No. 201810264813.X, filed on Mar. 28, 2018, and which incorporates by reference those PCT and Chinese applications in their entireties.

FIELD OF THE INVENTION

The present invention relates to the field of biotechnology and specifically, relates to a method for large-scale preparation of purified preparation of recombinant lentiviral vector at GMP grade.

BACKGROUND OF THE INVENTION

Gene therapy refers to the introduction of exogenous therapeutic genes into target cells to correct or compensate diseases caused by gene defects and abnormalities, or refers to using products expressed by exogenous genes to act on disease targets, thereby achieving the purpose of treatment. Exogenous genes can be transduced or delivered through viral or non-viral vectors. Commonly used non-viral vectors comprise liposome, dendrimer, non-natural cationic polymer and natural polysaccharide, etc. Non-viral gene delivery vectors are relatively safe and stable, but their transfection efficiency is usually low. Viral vectors encapsulate exogenous genes with the shell of natural viruses, and use the infectivity of virus against host cells to introduce exogenous genes into cells. Common viral vectors comprise recombinant retrovirus (rRV), recombinant lentivirus (rLV), recombinant adenovirus (rAd), and recombinant adeno-associated virus (rAAV), etc. The transduction efficiency of viral vectors is much higher than that of non-viral vectors, and is particularly suitable for infecting target cells that are difficult to be infected, such as lymphocytes.

Recombinant lentivirus vector is a gene therapy vector developed based on HIV-1 (Human Immunodeficiency Type I Virus). Different from the general retroviral vector, it has the ability to infect both dividing cells and non-dividing cells. Recombinant lentivirus vector has become the first transgenic vectors for CART cells and gene therapy due to its high biological titer and low immunogenicity in vivo and in vitro.

The current recombinant lentivirus vector is genetically modified to only retain the packaging signal and target gene transcripts in the lentiviral genome, while the structural genes such as reverse transcriptase, envelope protein VSVG and gag-pol are separated in 2 or 3 vectors, and disease-causing genes are removed simultaneously. Mature lentiviral particles are produced by co-transfecting 293T cells with multiple vectors and packaging in cells. The mature lentiviral particles are secreted by 293T cells into the culture supernatant, and are obtained by ultracentrifugation or chromatography methods.

The method used in conventional laboratories to obtain lentivirus is ultracentrifugation. Although this method is simple, it cannot be industrially used for large-scale production. The prepared lentivirus vector may have high residues of endotoxin, BSA, HCP or nucleic acid, and cannot be administrated directly into human body.

In addition, the existing chromatography purification methods also have the disadvantages of complicated steps, low yield and low purity, etc, and are hard to meet the requirements of industrialized large-scale preparation and GMP grade production.

Therefore, there is an urgent need in this field to develop a method for preparing purified lentivirus vector which is new, efficient, suitable to large-scale preparation and meets the requirements of GMP grade production.

SUMMARY OF THE INVENTION

The purpose of the present invention is to provide a method for preparing purified lentivirus vector which is efficient, suitable to large-scale preparation and meets the requirements of GMP grade production.

The another purpose of the present invention is to provide a recombinant lentivirus purified by the method, and a purified preparation comprising the recombinant lentivirus and the uses thereof.

In the first aspect of the present invention, it provides a method for large-scale purification of recombinant viral vector preparations, which comprises the following steps:
(a) providing a raw material comprising recombinant viral vectors to be purified, wherein the raw material is a feed liquid, and the volume of the feed liquid is Va;
(b) carrying out microfiltration treatment on the feed liquid to obtain a microfiltered filtrate comprising the recombinant viral vectors, and the volume of the filtrate is Vb;
(c) optionally concentrating the filtrate to obtain a concentrated filtrate, wherein the volume of the concentrated filtrate is Vc;
(d) purifying the filtrate obtained in the previous step by means of chromatography to obtain a crude pure product comprising the recombinant viral vectors;
(e) subjecting the crude pure product obtained in the previous step to liquid exchange and elaborate purification, thereby obtaining purified recombinant viral vectors;
wherein, the chromatography is selected from the group consisting of anion chromatography, size exclusion chromatography, multi-mode composite resin chromatography, and combinations thereof.

In another preferred embodiment, the Va≥100 L (or 100-500 L).

In another preferred embodiment, after step (e), the method further comprises:
(f) subjecting the purified recombinant viral vectors to liquid exchange to obtain a virus freezing solution comprising the recombinant viral vectors;
(g) sterilizing the virus after liquid exchange by filtration to obtain sterilized recombinant viral vectors.

In another preferred example, the virus comprises lentivirus.

In another preferred embodiment, the method meets GMP conditions.

In another preferred embodiment, in step (d), size exclusion chromatography and anion chromatography are performed sequentially, successively or simultaneously.

In another preferred embodiment, the anionic resin is selected from the group consisting of Capto Q, Capto ImpRes, and Capto DEAE.

In another preferred example, the multi-mode composite chromatography resin is selected from the group consisting of Capto adhere ImpRes, and Capto core 700.

In another preferred embodiment, the chromatography purification is to perform anion chromatography for crude purification firstly, and then perform multi-mode composite chromatography for elaborate purification.

In another preferred embodiment, the chromatography purification is to perform multi-mode composite chromatography for crude purification firstly, and then perform anion chromatography for elaborate purification.

In another preferred example, the chromatography purification process is to connect two types of multi-mode composite chromatography in series to simultaneously perform adsorption and removal of impurities and capture of viruses.

In another preferred embodiment, the chromatography purification time of the concentrated liquid is 10 L/30 min.

In another preferred example, the treatment speed of the chromatography purification is 20 L filtrate to be chromatographed per 60 minutes.

In another preferred example, the weight-volume ratio of the chromatography medium to the filtrate to be chromatographed is 500 mL:10 L filtrate.

In another preferred embodiment, the pore size of the filter for sterilization is 0.2 μM.

In another preferred embodiment, the chromatography medium is selected from the group consisting of Capto Q ImpRes.

In another preferred example, in step (d), the purified recombinant lentiviral vectors have one or more features selected from the following group:
(p1) the biological titer of recombinant lentiviral vectors is $1.0^6 \times 10^9$ Tu/mL;
(p2) the residue of BSA is <50 ng/mL;
(p3) the content of endotoxin is <1 EU/mL.

In another preferred embodiment, before the chromatography purification, the filtrate (comprising concentrated or non-concentrated filtrate) is subjected to nuclease treatment.

In another preferred embodiment, the nuclease treatment comprises: adding 10 U/ml nuclease and incubating at 37° C. for 30 min.

In another preferred embodiment, in step (b), the microfiltration treatment is carried out with a microfiltration hollow fiber column.

In another preferred embodiment, the microfiltration hollow fiber column is a microfiltration membrane with a cut-off value of 0.4-1.0 μm (preferably 0.45-0.8 μm).

In another preferred example, in step (c), the ratio of Vb to Vc (Vb/Vc) is 5-50, preferably 10-30, and more preferably 15-25.

In another preferred example, in step (c), the concentration is performed by ultrafiltration.

In another preferred embodiment, the ultrafiltration is performed by using an ultrafiltration membrane with a cut-off value of 100~800K.

In another preferred embodiment, the cut-off value of the ultrafiltration hollow fiber column is 200-1000K, and preferably 300-500K.

In another preferred embodiment, the ultrafiltration is performed by an ultrafiltration hollow fiber column and an ultrafiltration system.

In another preferred embodiment, the ultrafiltration system is selected from the group consisting of AKTA flux 6, and AKTA readyflux.

In the second aspect of the present invention, it provide a purified recombinant lentivirus prepared by the method.

In the third aspect of the present invention, it provides a preparation, which comprises the purified recombinant lentivirus.

In another preferred embodiment, the preparation is a pharmaceutical composition.

In another preferred embodiment, the pharmaceutical composition further comprises a pharmaceutically acceptable carrier.

In the fourth aspect of the present invention, it provides a purification device for the method, which comprises:
(S1) an optional first container, wherein the first container is used for holding raw material of recombinant lentivirus to be purified;
(S2) a microfiltration unit, wherein the microfiltration unit is used to perform microfiltration on the recombinant lentivirus to be purified to obtain a microfiltration filtrate;
(S3) an optional concentration unit, wherein the concentration unit is used to concentrate the filtrate to obtain a concentrated filtrate;
(S4) a chromatography purification unit, wherein the chromatography purification unit is used to perform chromatography purification on the filtrate from the microfiltration unit or the concentration unit to obtain a purified recombinant lentiviral vectors; and
(S5) a collection unit, wherein the collection unit is used to collect the purified recombinant lentiviral vector.

In another preferred embodiment, the first container, the microfiltration unit, the concentration unit, the chromatography purification unit and the collection unit are in liquid connection.

In another preferred example, the chromatography purification unit comprises a size exclusion chromatography unit and an anion chromatography unit.

In another preferred example, the size exclusion chromatography unit and the anion chromatography unit are independent.

In another preferred example, the size exclusion chromatography unit and the anion chromatography unit are integrated.

In another preferred example, the purification device further comprises:
(S6) a nuclease treatment unit, wherein the nuclease treatment unit comprises an adding device for adding nuclease.

In another preferred example, the nuclease treatment unit further comprises an incubation device for incubating the filtrate in which nuclease are added.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Based on extensive and intensive research, the inventors have firstly found a method for large-scale purification of recombinant lentivirus at GMP grade, which is fast and simple and has excellent purification effect. In the method of present invention, the raw material comprising recombinant lentivirus can be purified efficiently, rapidly and at large scale by using specific purification medium and specific purification steps and conditions, so as to prepare recombinant lentivirus preparation with high purity, less impurities and no endotoxin. On this basis, the invention is completed.

Terms

As used herein, the term "composite filler resin" refers to Capto Q, Capto ImpRes, Capto DEAE.

As used herein, the term "composite filler resin chromatography" refers to chromatography performed by using a composite filler resin.

As used herein, the terms "recombinant lentivirus", "lentiviral vector" can be used interchangeably, and refer to lentiviral vector produced by introducing specific plasmids into specific packaging cells. Typically, the lentiviral vectors can be used to transfect predetermined cells (comprising human and non-human mammalian cells) for subsequent therapeutic or non-therapeutic purposes.

The method described in the present invention can rapidly obtain high-purity lentivirus preparation by using (but not limited to) the combination of a new generation of Capto Core700 and Capto adhere ImpRes resin.

The purified preparation of the recombinant lentiviral vector prepared by the method of present invention can be used for the production of cells or gene medicines.

The main advantages of the present invention include:

High-purity lentivirus preparation can be quickly obtained by combining Capto Core700 and Capto adhere ImpRes for lentivirus purification.

The present invention will be further described below with reference to specific embodiments. It should be understood that these examples are only used to illustrate the present invention and not to limit the scope of the present invention. The experimental methods without specific conditions in the following examples are generally based on conventional conditions, such as Sambrook et al., Molecular Cloning: Laboratory Manual (New York: Cold Spring Harbor Laboratory Press, 1989) or as recommended by the manufacturer. Unless stated otherwise, percentages and parts are by weight.

EXAMPLE 1

(1) Harvesting feed liquid: lentivirus feed liquid was collected.
(2) Microfiltering and cleaning:
 a) 0.45-0.8 μM microfiltration hollow fiber column and AKTA Flux 6 system were connected, and the integrity was tested;
 b) AKTA Flux 6 system was sterilized by using 1M NaOH online;
 c) AKTA Flux 6 system was cleaned with injection water;
 d) AKTA Flux 6 system was cleaned by sterile 1×PBS;
 e) 20 L recombinant lentivirus feed liquid was divided into two aliquots and poured into feed liquid bucket. Microfiltration was performed, and the filtrate was harvested.
(3) Ultrafiltration and concentration:
 a) 300-800K ultrafiltration hollow fiber column was connected to AKTA Flux 6 system and the integrity was tested;
 b) AKTA Flux 6 system was sterilized by using 1M NaOH online;
 c) AKTA Flux 6 system was cleaned with injection water;
 d) AKTA Flux 6 system was cleaned by sterile 1×PBS;
 e) the microfiltered lentivirus feed liquid was ultrafiltered and concentrated by using 300-800K ultrafiltration column and AKTA Flux 6 system, and the filtrate was discard;
 f) the lentivirus feed liquid was concentrated from 20 L to 1~2 L.
(4) Nuclease treatment:
 a) nuclease was added into said 1~2 L lentivirus feed liquid at a ratio of 10~1000 U/mL and mixed completely;
 b) incubating overnight at 2-8° C.
(5) Capto Core700 and Capto adhere ImpRes connected in series were used to remove impurities and to capture viruses:
 a) 500 mL Capto Core700 and 500 mL Capto adhere ImpRes were connected in series and installed on the AKTA pure 150 chromatography system;
 b) AKTA Pure 150 system was sterilized by using 1M NaOH online;
 c) AKTA Pure 150 system was cleaned with injection water;
 d) sterile lentivirus freezing solution was loaded and passed through AKTA Pure 150 system;
 e) balancing;
 f) 1~2 L of feed liquid was loaded. After loading, 20~50 mM Tris-Cl/1~1.5M NaCl was used to elute, and elution peak was collected.
(6) Fluid exchange by Ultrafiltration
 a) 300-800K ultrafiltration hollow fiber column and AKTA Flux 6 system were connected and the integrity was tested;
 b) AKTA Flux 6 system was sterilized by using 1M NaOH online;
 c) AKTA Flux 6 system was cleaned with injection water;
 d) AKTA Flux 6 system was cleaned with sterile lentivirus freezing solution;
 e) the microfiltered lentivirus feed liquid was ultrafiltered for liquid exchange by using 300-800K ultrafiltration column and AKTA Flux 6 system, and the filtrate was discard;
 f) recombinant lentiviral vectors were harvested and volume thereof was 100~300 mL.
(7) Sterilization by filtration, packaging and frozen storage:
 a) the purified lentivirus feed liquid was filtered with 0.2 μM filter;
 b) the final product was packaged as 1 ml/tube preparation;
 c) the lentiviral preparations were stored at ultra-low temperature refrigerator ($\leftarrow$70° C.).

1. Results:
(1) The lentivirus final product had a concentration of $2\times10^9$ to $4\times10^9$ lentivirus/mL;
(2) BSA was <50 ng/mL;
(3) HCP was <1 ng/mL;
(4) the residue of nucleic acid was <5 pg/mL;
(5) RCL was negative.

2. Conclusion 0.45-0.8 μM microfiltration hollow fiber column, 300-800K hollow fiber column and Capto Core700+Capto adhere ImpRes composite filler were used stepwise for cleaning filtration, concentration, liquid exchange and removal of impurities and could quickly and effectively obtain high-purity lentivirus preparation.

All literatures mentioned in the present application are incorporated herein by reference, as though each is individually incorporated by reference. Additionally, it should be understood that after reading the above teachings, those skilled in the art can make various changes and modifications to the present invention. These equivalents also fall within the scope defined by the appended claims.

The invention claimed is:

1. A method for large-scale purification of recombinant viral vectors, wherein the method comprises:
   (a) providing a raw material comprising the recombinant viral vectors, wherein the raw material is a feed liquid, and wherein the feed liquid has a volume of no less than 20 liters;
   (b) carrying out microfiltration treatment on the feed liquid to obtain a microfiltered filtrate comprising the recombinant viral vectors, wherein the microfiltration treatment is conducted using a microfiltration hollow fiber column, wherein the microfiltration hollow fiber column comprises a microfiltration membrane with a cut-off value of 0.4 to 1.0 μm;
   (c) concentrating the filtrate to obtain a concentrated filtrate, wherein the concentrating is conducted using an ultrafiltration hollow fiber column with a cut-off value of 200 K to 1000 K;
   (d) purifying the filtrate by chromatography to obtain a crude product comprising the recombinant viral vectors; and
   (e) subjecting the crude product to liquid exchange and purification, thereby obtaining purified recombinant viral vectors;
   wherein the chromatography in step (d) is selected from the group consisting of anion chromatography, size exclusion chromatography, multi-mode composite resin chromatography, and combinations thereof.

2. The method of claim 1, wherein the chromatography in step (d) comprises anion chromatography, followed by multi-mode composite chromatography.

3. The method of claim 1, wherein after step (e), the method further comprises:
   (f) subjecting the purified recombinant viral vectors to liquid exchange to obtain a virus freezing solution comprising the recombinant viral vectors; and
   (g) sterilizing the virus freezing solution by filtration to obtain sterilized recombinant viral vectors.

4. The method of claim 1, wherein the recombinant viral vectors comprise lentiviral vectors.

5. The method of claim 1, wherein the filtrate obtained from step (b), or the concentrated filtrate obtained from step (c), is subjected to nuclease treatment before being purified by chromatography.

6. A purification device for performing the method of claim 1, which comprises:
   a microfiltration unit, wherein the microfiltration unit is used to perform microfiltration on the recombinant viral vectors to be purified to obtain a microfiltration filtrate;
   a concentration unit, wherein the concentration unit is used to concentrate the microfiltration filtrate to obtain a concentrated filtrate; and
   a chromatography purification unit, wherein the chromatography purification unit is used to perform chromatography purification on the concentrated filtrate to obtain purified recombinant lentiviral vectors.

7. The purification device of claim 6, wherein the chromatography purification unit comprises a size exclusion chromatography unit and an anion chromatography unit.

8. The purification device of claim 6, wherein the purification device further comprises:
   a nuclease treatment unit, wherein the nuclease treatment unit comprises an adding device for adding a nuclease.

* * * * *